US008938369B1

(12) United States Patent
Sobel (10) Patent No.: US 8,938,369 B1
(45) Date of Patent: Jan. 20, 2015

(54) SYSTEMS AND METHODS FOR ENSURING THAT CRITICAL COMPUTING DECISIONS ARE INTENTIONALLY MADE

(75) Inventor: William E. Sobel, Jamul, CA (US)

(73) Assignee: Symantec Corporation, Mountain View, CA (US)

( * ) Notice: Subject to any disclaimer, the term of this patent is extended or adjusted under 35 U.S.C. 154(b) by 981 days.

(21) Appl. No.: 13/048,122

(22) Filed: Mar. 15, 2011

(51) Int. Cl.
*G06F 19/00* (2011.01)

(52) U.S. Cl.
USPC .......................................... 702/182; 600/544

(58) Field of Classification Search
USPC ................................................. 600/544–546
See application file for complete search history.

(56) References Cited

U.S. PATENT DOCUMENTS

2001/0031930 A1* 10/2001 Roizen et al. ................. 600/544
2008/0177197 A1* 7/2008 Lee et al. ...................... 600/545

OTHER PUBLICATIONS

Freer Logic; Freer Logic, Improving Human Performance; http://www.freerlogic.com; Taken from site on Feb. 28, 2011.

* cited by examiner

*Primary Examiner* — Manuel L Barbee
(74) *Attorney, Agent, or Firm* — ALG Intellectual Property, LLC (57) ABSTRACT

A computer-implemented method for ensuring that critical computing decisions are intentionally made may include (1) detecting a request from a user to perform a computing act, (2) measuring, using a biofeedback sensor coupled to the computing device, physiological activity of the user that is indicative of a concentration level of the user, (3) determining, based on the measured physiological activity of the user, the user's concentration level, (4) identifying a requisite concentration level associated with the requested computing act, (5) determining whether the user's concentration level satisfies the requisite concentration level associated with the requested computing act, and then (6) preventing the requested computing act from occurring if the user's concentration level fails to satisfy the requisite concentration level associated with the requested computing act. Various other methods, systems, and computer-readable media are also disclosed.

20 Claims, 7 Drawing Sheets

SYSTEMS AND METHODS FOR ENSURING THAT CRITICAL COMPUTING DECISIONS ARE INTENTIONALLY MADE

BACKGROUND

User interfaces often present or request information to or from a user in a way that does not help the user reliably understand or determine the severity of their acts or decisions. For example, a user's incorrect answer to a user interface prompt may result in the accidental or unintentional deletion of years' worth of critical data. Similarly, an incorrect answer to a user interface prompt within an industrial-control environment may result in serious harm to others or other similarly disastrous consequences.

In view of the above, the instant disclosure identifies a need for improved user interfaces that ensure that critical computing decisions are knowingly and intentionally made by users.

SUMMARY

As will be described in greater detail below, the instant disclosure generally relates to systems and methods for ensuring that critical computing decisions are intentionally made. In one example, the systems described herein may accomplish such a task by (1) detecting a request from a user to perform a non-trivial computing act, (2) measuring, using a biofeedback sensor coupled to the computing device, physiological activity of the user (such as neural oscillations generated by the user's brain) that is indicative of the user's concentration level, (3) determining, based on the measured physiological activity of the user, the user's concentration level (e.g., whether the user is actively concentrating on the task at hand), (4) identifying a requisite concentration level associated with the requested computing act, (5) determining whether the user's current concentration level satisfies the requisite concentration level associated with the requested computing act, and then (6) preventing the requested computing act from occurring if the user's concentration level fails to satisfy the requisite concentration level associated with the requested computing act (e.g., if the user is not actively concentrating).

In some examples, the requested computing act may represent an act with non-trivial consequences, such that a user's approval and/or input may be required or desired prior to performing the computing act. In one embodiment, an application and/or operating system may generate a user interface prompt prior to performing the requested computing act in an attempt to ensure that the user knowingly and/or intentionally desired the results and/or consequences of the requested computing act. In this embodiment, the systems described herein may detect an attempt by the user to respond to the user interface prompt associated with the requested computing act.

In one example, the biofeedback sensor may represent an electroencephalograph (EEG) configured to measure electrical activity (such as the frequency of neural oscillations) produced by the user's brain. This biofeedback sensor may be worn by the user (e.g., as a headband or armband) or be integrally formed or affixed to an input device (such as mouse or keyboard) coupled to the computing device.

If the systems described herein determine that the user's concentration level fails to satisfy the requisite concentration level associated with the requested computing act, then the systems described herein may either attempt to raise the user's concentration level and/or simply prevent the requested computing act from occurring. The systems described herein may attempt to raise the user's concentration level in a variety of ways, including by generating and displaying a user interface prompt. In some examples, the systems described herein may display the user interface prompt until the user provides a desired response (such as, e.g., authentication credentials or an appropriate CAPTCHA response) or until the user's concentration level satisfies the requisite concentration level.

In an additional example, the systems described herein may dynamically modify at least one characteristic of the user interface prompt (such as the placement, text, size, color, and/or any other characteristic of the user interface prompt) in an attempt to raise the user's concentration level. These systems may also dynamically modify or tailor various characteristics of the user interface prompt based on the user's concentration level. For example, if an application or operating system presents a series of user interface prompts to a user in response to a request to perform a non-trivial computing act, then the systems described herein may dynamically modify various characteristics of one or more of these prompts if the concentration level of the user beings to wane.

As will be described in greater detail below, by actively monitoring the concentration level of a user, the systems and methods described herein may be able to ensure that critical computing decisions are intentionally and knowingly made by the user. As such, the systems and methods described herein may enable users and/or employers to reduce instances of user error, potentially avoiding the negative consequences of undesired or unintentional computing acts.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

Figure 1:
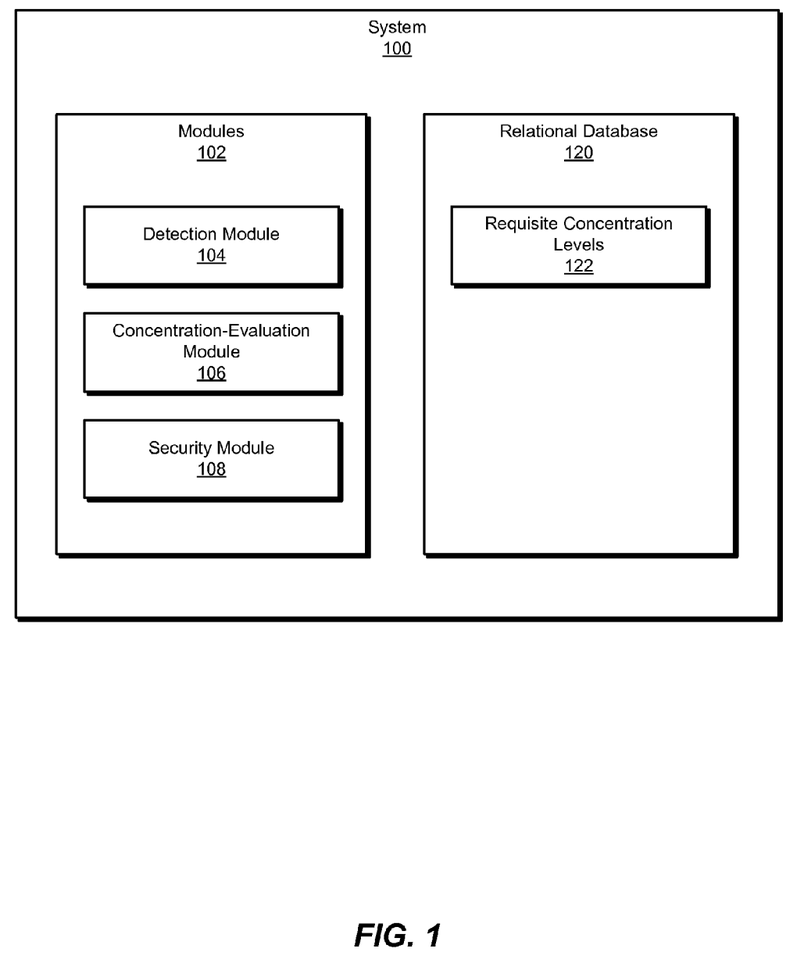
FIG. 1 is a block diagram of an exemplary system for ensuring that critical computing decisions are intentionally made.
Figure 2:
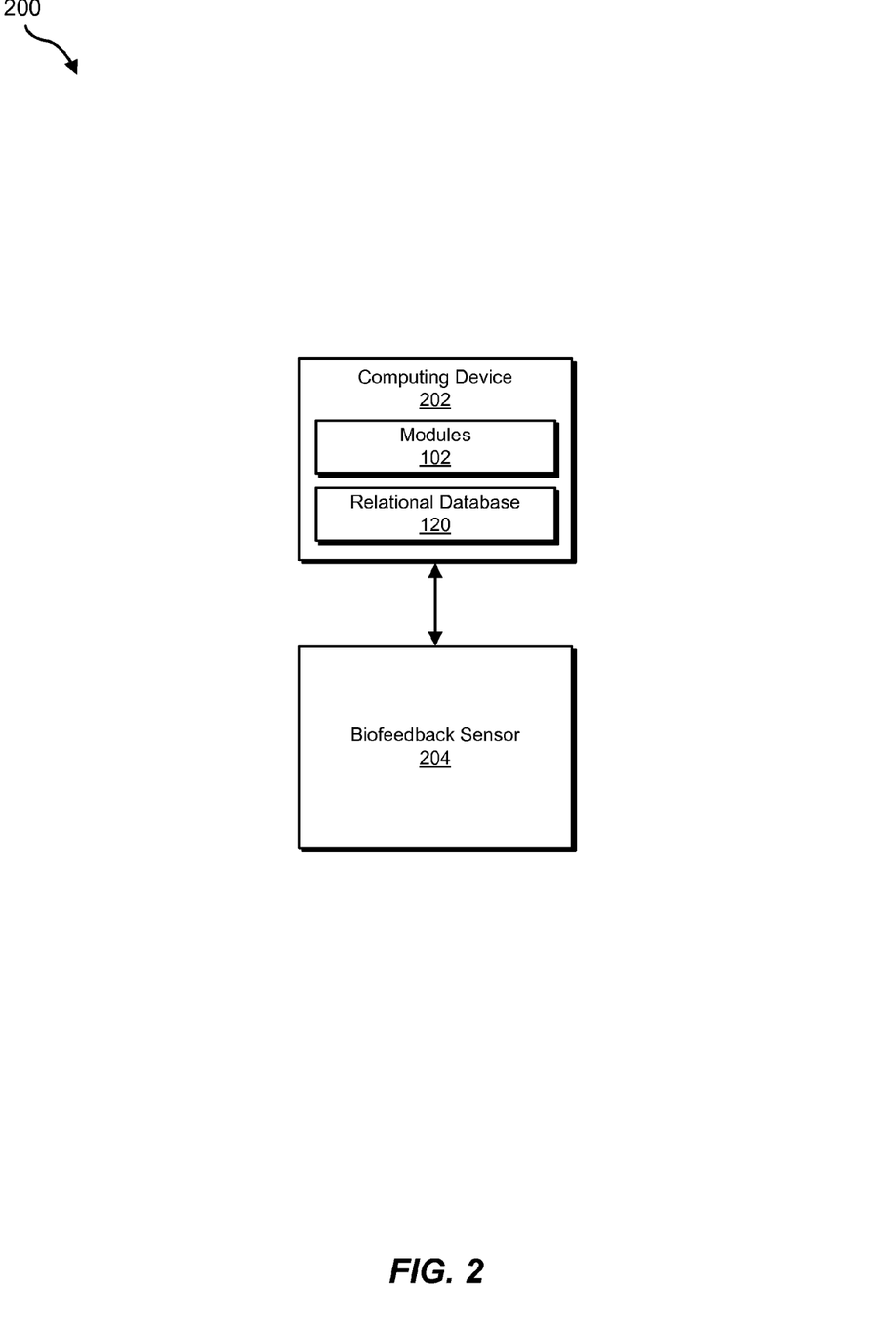
FIG. 2 is a block diagram of an exemplary system for ensuring that critical computing decisions are intentionally made.

The following will provide, with reference to FIGS. 1-2, detailed descriptions of exemplary systems for ensuring that critical computing decisions are intentionally made. Detailed descriptions of corresponding computer-implemented methods will also be provided in connection with FIGS. 3-5. In addition, detailed descriptions of an exemplary computing system and network architecture capable of implementing one or more of the embodiments described herein will be provided in connection with FIGS. 6 and 7, respectively.

FIG. 1 is a block diagram of an exemplary system 100 for ensuring that critical computing decisions are intentionally made. As illustrated in this figure, exemplary system 100 may include one or more modules 102 for performing one or more tasks. For example, and as will be explained in greater detail below, exemplary system 100 may include a detection module 104 programmed to detect a request from a user to perform a non-trivial computing act on a computing device. Exemplary system 100 may also include a concentration-evaluation module 106 programmed to (1) measure, using a biofeedback sensor coupled to the computing device, physiological activity of the user that is indicative of a concentration level of the user, (2) determine the user's concentration level based on the measured physiological activity of the user, (3) identify a requisite concentration level associated with the requested computing act, and then (4) determine whether the user's concentration level satisfies the requisite concentration level associated with the requested computing act.

In addition, and as will be described in greater detail below, exemplary system 100 may include a security module 108 programmed to prevent the requested computing act from occurring if the user's concentration level fails to satisfy the requisite concentration level associated with the requested computing act. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, as will be described in greater detail below, one or more of modules 102 may represent software modules stored and configured to run on one or more computing devices, such as the devices illustrated in FIG. 2 (e.g., computing device 202 and/or biofeedback sensor 204), computing system 610 in FIG. 6, and/or portions of exemplary network architecture 700 in FIG. 7. One or more of modules 102 in FIG. 1 may also represent all or portions of one or more special-purpose computers configured to perform one or more tasks.

As illustrated in FIG. 1, exemplary system 100 may also include one or more databases, such as relational database 120. In one example, and as will be described in greater detail below, relational database 120 may be configured to store a threshold or requisite concentration level (e.g., requisite concentration levels 122) for one or more non-trivial computing acts that may be performed by a computing device (e.g., computing device 202). Relational database 120 may represent portions of a single database or computing device or a plurality of databases or computing devices. For example, relational database 120 may represent a portion of computing device 202 in FIG. 2, computing system 610 in FIG. 6, and/or portions of exemplary network architecture 700 in FIG. 7. Alternatively, relational database 120 in FIG. 1 may represent one or more physically separate devices capable of being accessed by a computing device, such as computing device 202 in FIG. 2, computing system 610 in FIG. 6, and/or portions of exemplary network architecture 700 in FIG. 7.

Exemplary system 100 in FIG. 1 may be deployed in a variety of ways. For example, all or a portion of exemplary system 100 may represent portions of exemplary system 200 in FIG. 2. As shown in FIG. 2, system 200 may include a computing device 202 coupled to a biofeedback sensor 204. In one embodiment, and as will be described in greater detail below, modules 102 may program computing device 202 to ensure that critical computing decisions are intentionally made by (1) detecting a request from a user (e.g., a user of computing device 202) to perform a computing act, (2) measuring, using a biofeedback sensor (e.g., biofeedback sensor 204) coupled to the computing device, physiological activity of the user that is indicative of a concentration level of the user, (3) determining, based on the measured physiological activity of the user, the user's concentration level, (4) identifying a requisite concentration level associated with the requested computing act (stored, e.g., within relational database 120), (5) determining whether the user's concentration level satisfies the requisite concentration level associated with the requested computing act, and then (6) preventing the requested computing act from occurring if the user's concentration level fails to satisfy the requisite concentration level associated with the requested computing act.

Computing device 202 generally represents any type or form of computing device capable of reading computer-executable instructions. Examples of computing device 202 include, without limitation, laptops, desktops, servers, cellular phones, personal digital assistants (PDAs), multimedia players, embedded systems, combinations of one or more of the same, exemplary computing system 610 in FIG. 6, or any other suitable computing device.

Biofeedback sensor 204 generally represents any type or form of sensor capable of measuring or monitoring any type or form of physiological activity, including physiological activity that may be indicative of a user's concentration level. In some examples, biofeedback sensor 204 may be worn by a user of computing device 202 (e.g., as a headband or armband) and coupled (via wired or wireless technology) to computing device 202. In other examples, biofeedback sensor 204 may represent a portion of a user input device (such as a keyboard or mouse) coupled to computing device 202. For example, biofeedback sensor 204 may represent a sensor that is integrally formed or fixed to a mouse coupled to computing device 202.

Figure 3:
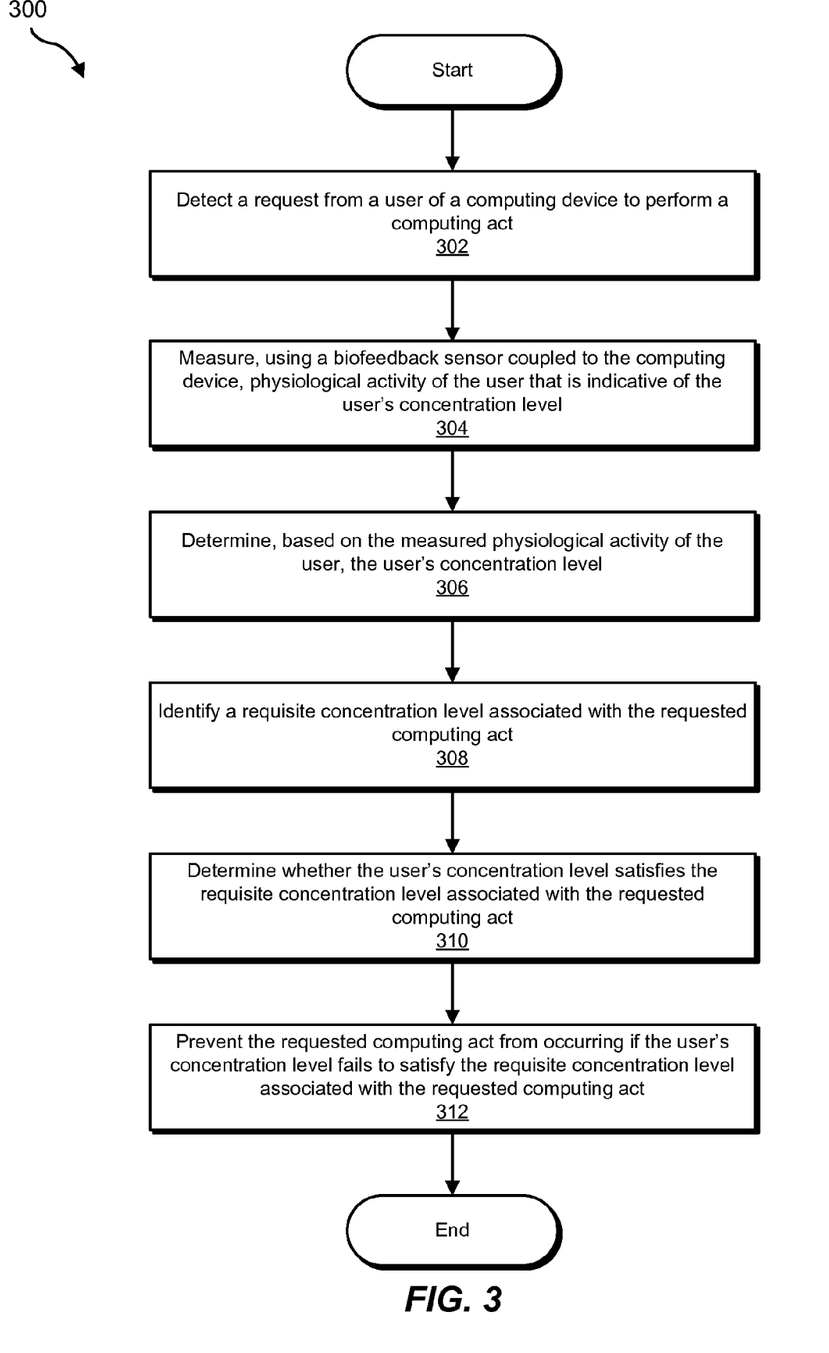
FIG. 3 is a flow diagram of an exemplary method for ensuring that critical computing decisions are intentionally made.
Figure 4:
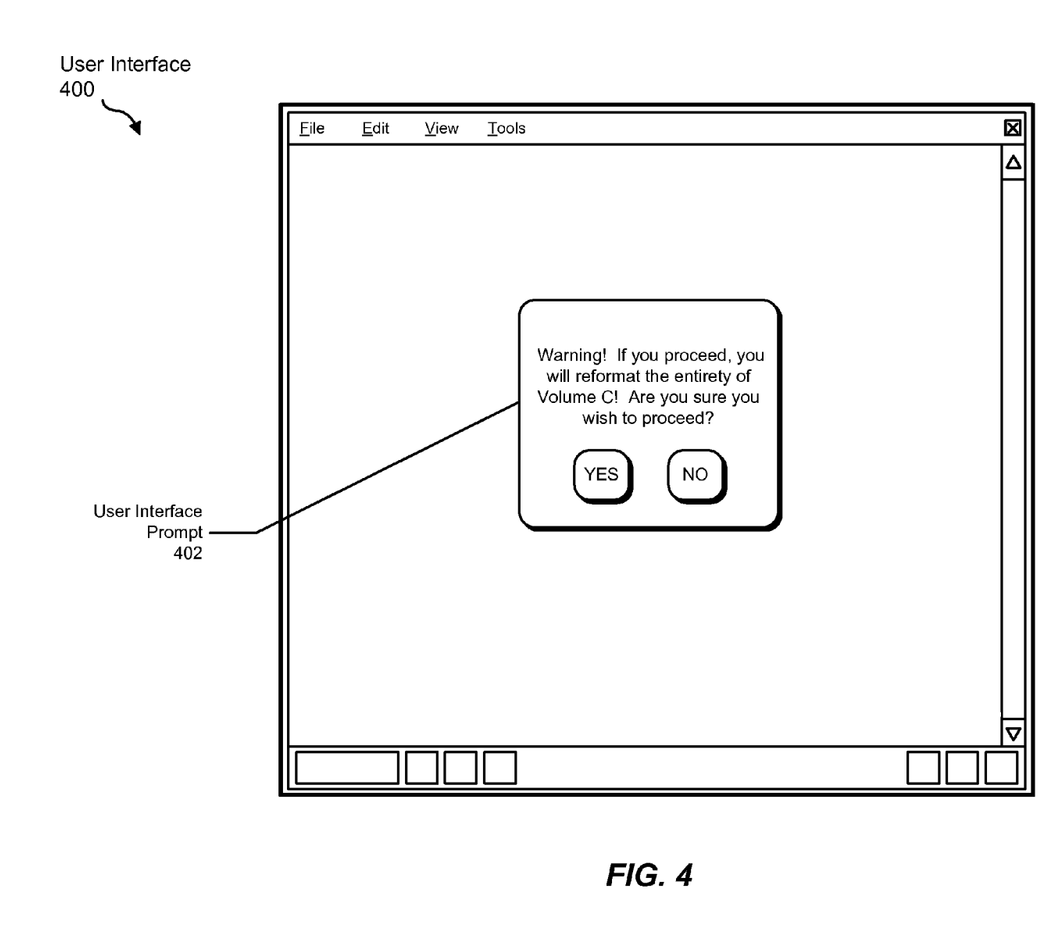
FIG. 4 is a block diagram of an exemplary user interface prompt.

FIG. 3 is a flow diagram of an exemplary computer-implemented method 300 for ensuring that critical computing decisions are intentionally made. The steps shown in FIG. 3 may be performed by any suitable computer-executable code and/or computing system. In some embodiments, the steps shown in FIG. 3 may be performed by one or more of the components of system 100 in FIG. 1, system 200 in FIG. 2, computing system 610 in FIG. 6, and/or portions of exemplary network architecture 700 in FIG. 7.

As illustrated in this figure, at step 302 the systems described herein may detect a request from a user to perform a computing act. For example, detection module 104 may, as part of computing device 202 in FIG. 2, detect a request from a user of computing device 202 to perform a non-trivial computing act.

The phrase "computing act," as used herein, may refer to any type or form of action performed by, or in connection with, a computing device. In some examples, a "computing act" may refer to an act with non-trivial consequences, such that a user's approval and/or input may be required or desired prior to performing the computing act in order to ensure that the user knowingly and intentionally desires the results of requested computing act. Examples of such computing acts include, without limitation, acts that impact the stability, performance, and/or security of a computing device (e.g., attempts to download or access untrusted or malicious files, attempts to open a hole in a device's firewall, attempts to delete files and/or reformat storage devices, or the like), acts that may be prone to user error (e.g., repetitive acts or acts that require trivial user input to perform), acts that may impact the user's safety (e.g., industrial-control events), or any other computing act (such as service-desk conformation prompts) for which a user's input, authorization, and/or approval may be required or desired (in order to ensure, e.g., that the user knowingly and intentionally desires the results of requested computing act).

The systems described herein may perform step 302 in a variety of ways and/or contexts. In one example, step 302 (along with one or more additional steps of exemplary method 300 in FIG. 3) may be implemented at the application and/or operating-system level. Specifically, detection module 104 (along with the remainder of modules 102 in FIG. 1) may represent a portion (e.g., as an API) of an application or operating system installed on computing device 202. In this example, detection module 104 may maintain a list of non-trivial computing acts that are to be monitored and may monitor (using, e.g., a filter driver) computing device 202 for attempts to perform any of the computing acts on this list.

In some examples, the systems described herein may perform step 302 by detecting an attempt by the user to respond to a user interface prompt associated with the requested computing act. For example, detection module 104 may detect an attempt by a user of computing device 202 to respond to a user interface prompt 402 in FIG. 4 generated by an application and/or operating system in an attempt to ensure that the user knowingly and/or intentionally desires the results and/or consequences of the requested computing act (in this example, the reformatting of volume C on computing device 202).

Returning to FIG. 3, at step 304 the systems described herein may measure, using a biofeedback sensor coupled to the computing device, physiological activity of the user that is indicative of a concentration level of the user. For example, concentration-evaluation module 106 may, as part of computing device 202 in FIG. 2, measure (using biofeedback sensor 204) physiological activity of a user of computing device 202 that is indicative of the user's concentration level.

The phrase "concentration level," as used herein, may refer to a user's current state of awareness, as measured using various quantifiable metrics. Examples of the types of physiological activity that may be measured to determine a user's concentration level include, without limitation, electrical activity produced by the user's brain (including, e.g., the frequencies of neural oscillations produced by the user's brain), the user's heart rate, the user's blood pressure, the user's retinal activity, the user's breath rate, or any other physiological activity that may be indicative of the user's concentration level. For example, in one embodiment biofeedback sensor 204 may represent an EEG configured to measure electrical activity produced by the brain of a user of computing device 202.

As detailed above, biofeedback sensor 204 in FIG. 2 generally represents any type or form of sensor capable of measuring or monitoring any type or form of physiological activity that may be indicative of a user's concentration level. In some examples, biofeedback sensor 204 may be worn by the user of computing device 202 (e.g., as a headband or armband) and coupled (via wired or wireless technology) to computing device 202. In other examples, biofeedback sensor 204 may represent a portion of a user input device (such as a keyboard or mouse) coupled to computing device 202. For example, biofeedback sensor 204 may represent a sensor that is integrally formed or fixed to a mouse coupled to computing device 202.

Returning to FIG. 3, at step 306 the systems described herein may determine the user's concentration level based on the measured physiological activity of the user. For example, concentration-evaluation module 106 may, as part of computing device 202 in FIG. 2, determine the user's concentration level based on the physiological activity measured in step 304.

The systems described herein may perform step 306 in a variety of ways. In one example, if step 304 involved measuring the frequencies of neural oscillations produced by the user's brain, then in step 306 the systems described herein may map the measured frequencies to a generally accepted scale of user awareness or concentration. One such generally accepted neurological scale specifies that neural oscillations measured in the 12 to 30 Hz frequency range (also commonly referred to as "beta waves") are indicative of a user that is consciously alert or actively concentrating, while neural oscillations measured in the 8 to 12 Hz frequency range (commonly referred to as "alpha waves") or 4 to 8 Hz frequency range ("commonly referred to as theta waves") are indicative of a user that is in a state of mental relaxation or reduced consciousness, respectively. In this example, concentration-evaluation module 106 may determine that a user is actively concentrating if, in step 304, biofeedback sensor 204 measured neural oscillations generated by the user's brain that fall within the 12 to 30 Hz frequency range. In contrast, concentration-evaluation module 106 may determine that the user is not actively concentrating if, in step 304, biofeedback sensor 204 measured neural oscillations generated by the user's brain that fall within the 4 to 8 Hz or 8 to 12 Hz frequency range.

Returning to FIG. 3, at step 308 the systems described herein may identify a requisite concentration level associated with the requested computing act. For example, concentration-evaluation module 106 may, as part of computing device 202 in FIG. 2, identify a threshold or requisite concentration level within relational database 120 that is associated with the requested computing act detected in step 302.

The systems described herein may perform step 308 in a variety of ways. In one example, the systems described herein may maintain a relational database (e.g., relational database 120 in FIG. 1) that identifies a threshold or requisite concentration level (e.g., requisite concentration levels 122) for one or more non-trivial computing acts that may be performed by the computing device (i.e., for computing acts that produce results or consequences for which a user's input and/or authorization may be desired or required in order to ensure that the user intentionally or knowingly approved or requested performance of the computing act in question).

In the above example, if in step 302 detection module 104 detects a request by a user to perform a computing act (such as an attempt to reformat a volume of computing device 202) that is identified within relational database 120, then in step 308 concentration-evaluation module 106 may identify a requisite or threshold concentration level associated with the requested computing act within relational database 120. In this example, concentration-evaluation module 106 may determine that a user must be actively concentrating (as indicated by neural oscillations generated by the user's brain in the 12 to 30 Hz frequency range) in order for the requested reformatting act to be allowed or permitted.

Returning to FIG. 3, at step 310 the systems described herein may determine whether the user's concentration level satisfies the requisite concentration level associated with the requested computing act. For example, concentration-evaluation module 106 may, as part of computing device 202 in FIG. 2, determine whether the user's concentration level measured in step 306 satisfies the requisite or threshold concentration level identified in step 308.

The systems described herein may perform step 310 in a variety of ways. In one example, the systems described herein may determine whether the physiological activity measured in step 304 satisfies various criteria related to the requisite or threshold contemplation level identified in step 308. For example, concentration-evaluation module 106 may determine that a user is actively concentrating on the task at hand, and thus satisfies the requisite or threshold concentration level identified in step 308, if neural oscillations generated by the user's brain (as measured in step 304) fall within the frequency range of 12 to 30 Hz. In contrast, concentration-evaluation module 106 may determine that a user is not actively concentrating, such that the user's concentration level fails to satisfy the requisite or threshold concentration level identified in step 308, if neural oscillations generated by the user's brain and measured in step 304 fall within the 4 to 12 Hz frequency range.

Returning to FIG. 3, at step 312 the systems described herein may prevent the requested computing act from occurring if the user's concentration level fails to satisfy the requisite concentration level associated with the requested computing act. For example, security module 108 may, as part of computing device 202 in FIG. 2, prevent the requested computing act detected in step 302 from occurring if the user's concentration level determined in step 306 fails to satisfy the requisite concentration level identified in step 308.

The systems described herein may perform step 312 in a variety of ways and contexts. In one example, the systems described herein may allow the requested computing act to occur if the user's concentration level satisfies the requisite concentration level associated with the requested computing act. For example, if concentration-evaluation module 106 determines that the user's concentration level satisfies the requisite or threshold concentration level identified in step 308, then security module 108 may allow the requested computing act detected in step 302 to occur.

In contrast, if the systems described herein determine that a user's concentration level fails to satisfy the requisite concentration level associated with the requested computing act, then the systems described herein may attempt to raise the user's concentration level and/or simply prevent the requested computing act from occurring. For example, if concentration-evaluation module 106 determines in step 310 that a user's concentration level fails to satisfy the requisite or threshold concentration level identified in step 308 (or, alternatively, if biofeedback sensor 204 is not active or present), then security module 108 may attempt to raise the user's concentration level and/or simply prevent the requested computing act from occurring.

Security module 108 may attempt to raise a user's concentration level in a variety of ways. In one example, security module 108 may generate and display a user interface prompt, such as user interface prompt 402 in FIG. 4. In some examples, security module 108 may display the user interface prompt until the user provides a desired response (such as, e.g., authentication credentials or an appropriate CAPTCHA response) or until the user's concentration level satisfies the requisite or threshold concentration level identified in step 308.

Figure 5:
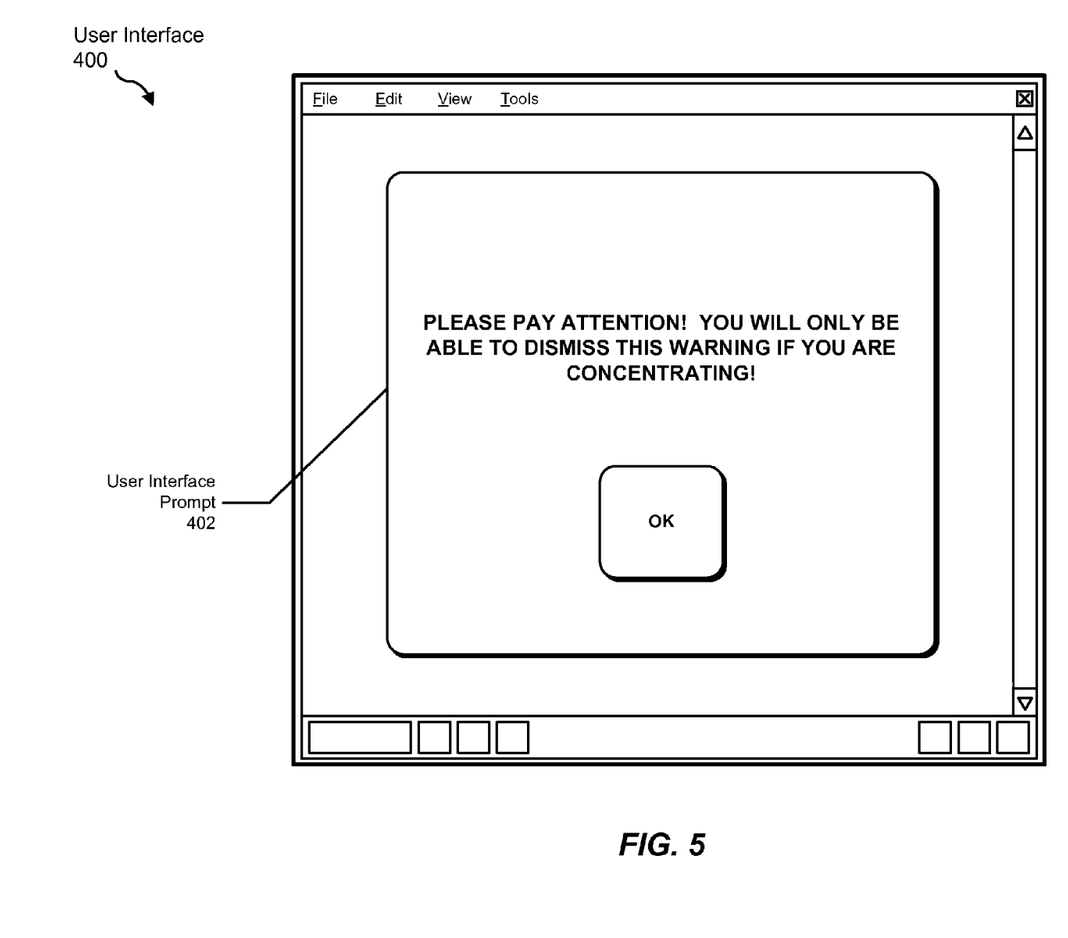
FIG. 5 is a block diagram of an exemplary modified user interface prompt.

In an additional example, security module 108 may attempt to raise the user's concentration level by dynamically modifying at least one characteristic of the user interface prompt. For example, and as illustrated in FIG. 5, security module 108 may modify the placement, text, size, color, and/or any other characteristic of user interface prompt 402 in an attempt to raise the user's concentration level.

In one example, security module 108 may dynamically modify or tailor various characteristics of the user interface prompt based on the user's concentration level. For example, if an application or operating system presents a series of user interface prompts to a user in response to a request to perform a non-trivial computing act, then security module 108 may dynamically modify various characteristics of one or more of these prompts if concentration-evaluation module 106 determines that the concentration level of the user is waning. Upon completion of step 312, exemplary method 300 in FIG. 3 may terminate.

As detailed above, by actively monitoring the concentration level of a user, the systems and methods described herein may be able to ensure that critical computing decisions are intentionally and knowingly made by the user. As such, the systems and methods described herein may enable users and/or employers to reduce instances of user error, potentially avoiding the negative consequences of undesired or unintentional computing acts.

Figure 6:
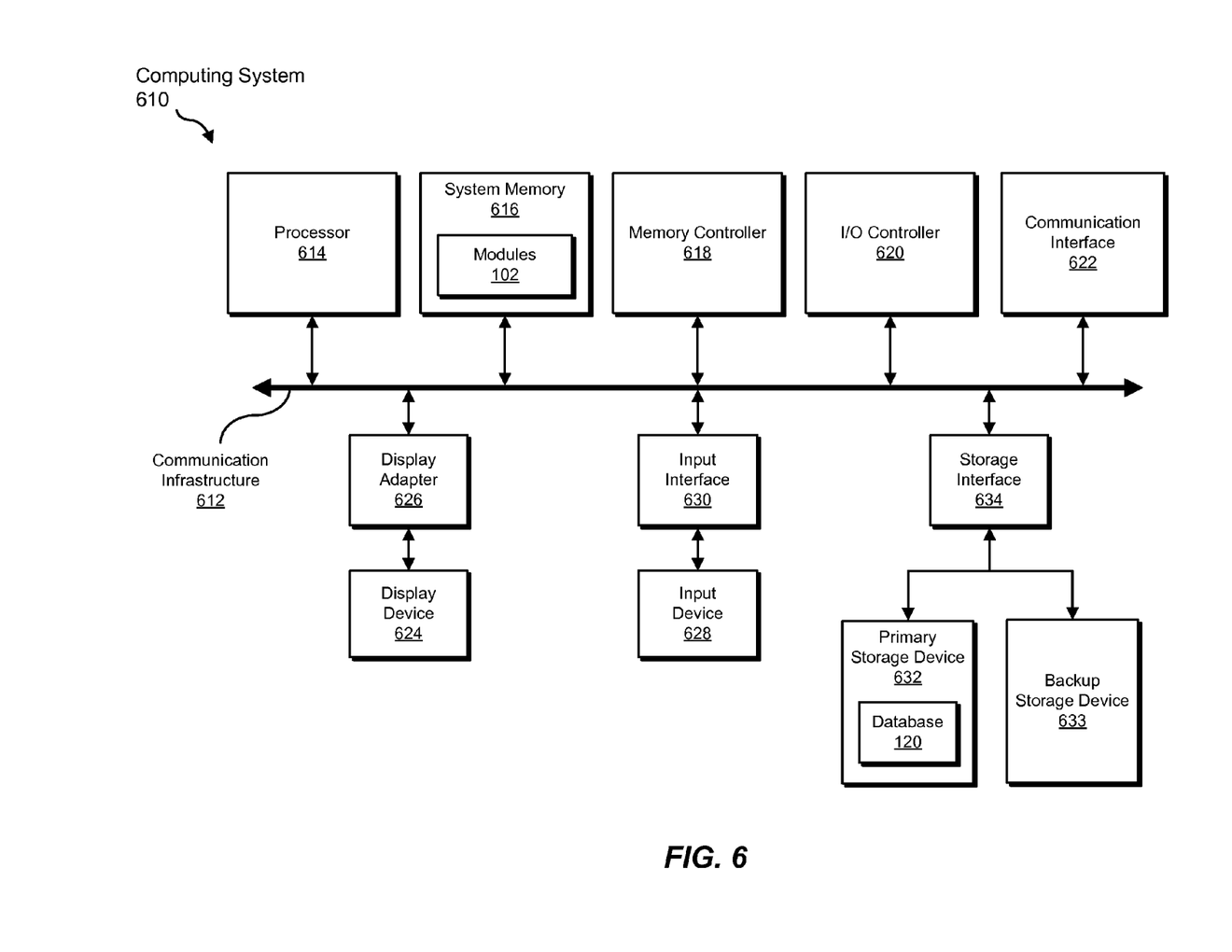
FIG. 6 is a block diagram of an exemplary computing system capable of implementing one or more of the embodiments described and/or illustrated herein.

FIG. 6 is a block diagram of an exemplary computing system 610 capable of implementing one or more of the embodiments described and/or illustrated herein. Computing system 610 broadly represents any single or multi-processor computing device or system capable of executing computer-readable instructions. Examples of computing system 610 include, without limitation, workstations, laptops, client-side terminals, servers, distributed computing systems, handheld devices, or any other computing system or device. In its most basic configuration, computing system 610 may include at least one processor 614 and a system memory 616.

Processor 614 generally represents any type or form of processing unit capable of processing data or interpreting and executing instructions. In certain embodiments, processor 614 may receive instructions from a software application or module. These instructions may cause processor 614 to perform the functions of one or more of the exemplary embodiments described and/or illustrated herein. For example, processor 614 may perform and/or be a means for performing, either alone or in combination with other elements, one or more of the detecting, measuring, using, determining, identifying, preventing, displaying, and modifying steps described herein. Processor 614 may also perform and/or be a means for performing any other steps, methods, or processes described and/or illustrated herein.

System memory 616 generally represents any type or form of volatile or non-volatile storage device or medium capable of storing data and/or other computer-readable instructions. Examples of system memory 616 include, without limitation, random access memory (RAM), read only memory (ROM), flash memory, or any other suitable memory device. Although not required, in certain embodiments computing system 610 may include both a volatile memory unit (such as, for example, system memory 616) and a non-volatile storage device (such as, for example, primary storage device 632, as described in detail below). In one example, one or more of modules 102 from FIG. 1 may be loaded into system memory 616.

In certain embodiments, exemplary computing system 610 may also include one or more components or elements in addition to processor 614 and system memory 616. For example, as illustrated in FIG. 6, computing system 610 may include a memory controller 618, an Input/Output (I/O) controller 620, and a communication interface 622, each of which may be interconnected via a communication infrastructure 612. Communication infrastructure 612 generally represents any type or form of infrastructure capable of facilitating communication between one or more components of a computing device. Examples of communication infrastructure 612 include, without limitation, a communication bus (such as an ISA, PCI, PCIe, or similar bus) and a network.

Memory controller 618 generally represents any type or form of device capable of handling memory or data or controlling communication between one or more components of computing system 610. For example, in certain embodiments memory controller 618 may control communication between processor 614, system memory 616, and I/O controller 620 via communication infrastructure 612. In certain embodiments, memory controller 618 may perform and/or be a means for performing, either alone or in combination with other elements, one or more of the steps or features described and/or illustrated herein, such as detecting, measuring, using, determining, identifying, preventing, displaying, and modifying.

I/O controller 620 generally represents any type or form of module capable of coordinating and/or controlling the input and output functions of a computing device. For example, in certain embodiments I/O controller 620 may control or facilitate transfer of data between one or more elements of computing system 610, such as processor 614, system memory 616, communication interface 622, display adapter 626, input interface 630, and storage interface 634. I/O controller 620 may be used, for example, to perform and/or be a means for performing, either alone or in combination with other elements, one or more of the detecting, measuring, using, determining, identifying, preventing, displaying, and modifying steps described herein. I/O controller 620 may also be used to perform and/or be a means for performing other steps and features set forth in the instant disclosure.

Communication interface 622 broadly represents any type or form of communication device or adapter capable of facilitating communication between exemplary computing system 610 and one or more additional devices. For example, in certain embodiments communication interface 622 may facilitate communication between computing system 610 and a private or public network including additional computing systems. Examples of communication interface 622 include, without limitation, a wired network interface (such as a network interface card), a wireless network interface (such as a wireless network interface card), a modem, and any other suitable interface. In at least one embodiment, communication interface 622 may provide a direct connection to a remote server via a direct link to a network, such as the Internet. Communication interface 622 may also indirectly provide such a connection through, for example, a local area network (such as an Ethernet network), a personal area network, a telephone or cable network, a cellular telephone connection, a satellite data connection, or any other suitable connection.

In certain embodiments, communication interface 622 may also represent a host adapter configured to facilitate communication between computing system 610 and one or more additional network or storage devices via an external bus or communications channel. Examples of host adapters include, without limitation, SCSI host adapters, USB host adapters, IEEE 1394 host adapters, SATA and eSATA host adapters, ATA and PATA host adapters, Fibre Channel interface adapters, Ethernet adapters, or the like. Communication interface 622 may also allow computing system 610 to engage in distributed or remote computing. For example, communication interface 622 may receive instructions from a remote device or send instructions to a remote device for execution. In certain embodiments, communication interface 622 may perform and/or be a means for performing, either alone or in combination with other elements, one or more of the detecting, measuring, using, determining, identifying, preventing, displaying, and modifying steps disclosed herein. Communication interface 622 may also be used to perform and/or be a means for performing other steps and features set forth in the instant disclosure.

As illustrated in FIG. 6, computing system 610 may also include at least one display device 624 coupled to communication infrastructure 612 via a display adapter 626. Display device 624 generally represents any type or form of device capable of visually displaying information forwarded by display adapter 626. Similarly, display adapter 626 generally represents any type or form of device configured to forward graphics, text, and other data from communication infrastructure 612 (or from a frame buffer, as known in the art) for display on display device 624.

As illustrated in FIG. 6, exemplary computing system 610 may also include at least one input device 628 coupled to communication infrastructure 612 via an input interface 630. Input device 628 generally represents any type or form of input device capable of providing input, either computer or human generated, to exemplary computing system 610. Examples of input device 628 include, without limitation, a keyboard, a pointing device, a speech recognition device, or any other input device. In at least one embodiment, input device 628 may perform and/or be a means for performing, either alone or in combination with other elements, one or more of the detecting, measuring, using, determining, identifying, preventing, displaying, and modifying steps disclosed herein. Input device 628 may also be used to perform and/or be a means for performing other steps and features set forth in the instant disclosure.

As illustrated in FIG. 6, exemplary computing system 610 may also include a primary storage device 632 and a backup storage device 633 coupled to communication infrastructure 612 via a storage interface 634. Storage devices 632 and 633 generally represent any type or form of storage device or medium capable of storing data and/or other computer-readable instructions. For example, storage devices 632 and 633 may be a magnetic disk drive (e.g., a so-called hard drive), a solid state drive, a floppy disk drive, a magnetic tape drive, an optical disk drive, a flash drive, or the like. Storage interface 634 generally represents any type or form of interface or device for transferring data between storage devices 632 and 633 and other components of computing system 610. In one example, database 120 from FIG. 1 may be stored in primary storage device 632.

In certain embodiments, storage devices 632 and 633 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 632 and 633 may also include other similar structures or devices for allowing computer software, data, or other computer-readable instructions to be loaded into computing system 610. For example, storage devices 632 and 633 may be configured to read and write software, data, or other computer-readable information. Storage devices 632 and 633 may also be a part of computing system 610 or may be a separate device accessed through other interface systems.

In certain embodiments, storage devices 632 and 633 may be used, for example, to perform and/or be a means for performing, either alone or in combination with other elements, one or more of the detecting, measuring, using, determining, identifying, preventing, displaying, and modifying steps disclosed herein. Storage devices 632 and 633 may also be used to perform and/or be a means for performing other steps and features set forth in the instant disclosure.

Many other devices or subsystems may be connected to computing system 610. Conversely, all of the components and devices illustrated in FIG. 6 need not be present to practice the embodiments described and/or illustrated herein. The devices and subsystems referenced above may also be interconnected in different ways from that shown in FIG. 6. Computing system 610 may also employ any number of software, firmware, and/or hardware configurations. For example, one or more of the exemplary embodiments disclosed herein may be encoded as a computer program (also referred to as computer software, software applications, computer-readable instructions, or computer control logic) on a computer-readable medium. The phrase "computer-readable medium" generally refers to any form of device, carrier, or medium capable of storing or carrying computer-readable instructions. Examples of computer-readable media include, without limitation, transmission-type media, such as carrier waves, and physical media, such as magnetic-storage media (e.g., hard disk drives and floppy disks), optical-storage media (e.g., CD- or DVD-ROMs), electronic-storage media (e.g., solid-state drives and flash media), and other distribution systems.

The computer-readable medium containing the computer program may be loaded into computing system 610. All or a portion of the computer program stored on the computer-readable medium may then be stored in system memory 616 and/or various portions of storage devices 632 and 633. When executed by processor 614, a computer program loaded into computing system 610 may cause processor 614 to perform and/or be a means for performing the functions of one or more of the exemplary embodiments described and/or illustrated herein. Additionally or alternatively, one or more of the exemplary embodiments described and/or illustrated herein may be implemented in firmware and/or hardware. For example, computing system 610 may be configured as an application specific integrated circuit (ASIC) adapted to implement one or more of the exemplary embodiments disclosed herein.

Figure 7:
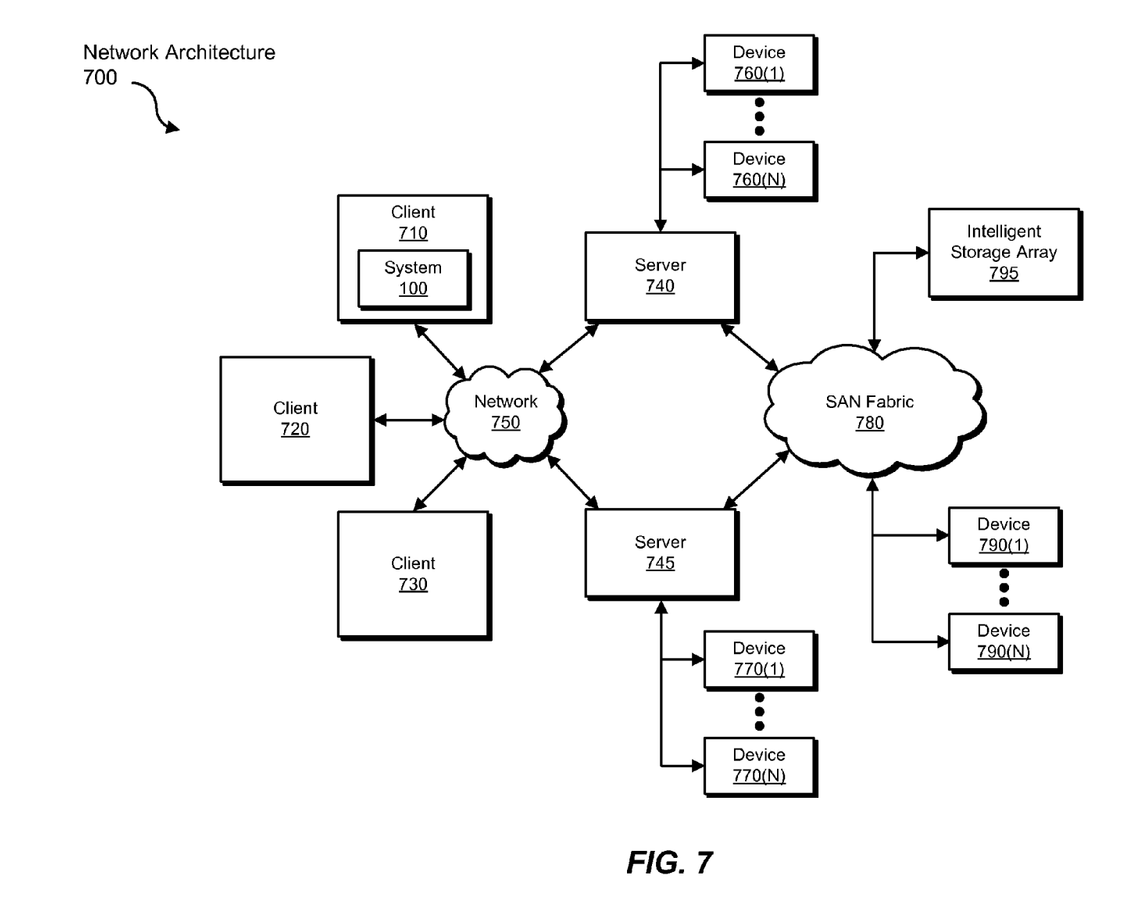
FIG. 7 is a block diagram of an exemplary computing network capable of implementing one or more of the embodiments described and/or illustrated herein.

FIG. 7 is a block diagram of an exemplary network architecture 700 in which client systems 710, 720, and 730 and servers 740 and 745 may be coupled to a network 750. Client systems 710, 720, and 730 generally represent any type or form of computing device or system, such as exemplary computing system 610 in FIG. 6.

Similarly, servers 740 and 745 generally represent computing devices or systems, such as application servers or database servers, configured to provide various database services and/or run certain software applications. Network 750 generally represents any telecommunication or computer network including, for example, an intranet, a wide area network (WAN), a local area network (LAN), a personal area network (PAN), or the Internet. In one example, client systems 710, 720, and/or 730 and/or servers 740 and/or 745 may include system 100 from FIG. 1.

As illustrated in FIG. 7, one or more storage devices 760 (1)-(N) may be directly attached to server 740. Similarly, one or more storage devices 770(1)-(N) may be directly attached to server 745. Storage devices 760(1)-(N) and storage devices 770(1)-(N) generally represent any type or form of storage device or medium capable of storing data and/or other computer-readable instructions. In certain embodiments, storage devices 760(1)-(N) and storage devices 770(1)-(N) may represent network-attached storage (NAS) devices configured to communicate with servers 740 and 745 using various protocols, such as NFS, SMB, or CIFS.

Servers 740 and 745 may also be connected to a storage area network (SAN) fabric 780. SAN fabric 780 generally represents any type or form of computer network or architecture capable of facilitating communication between a plurality of storage devices. SAN fabric 780 may facilitate communication between servers 740 and 745 and a plurality of storage devices 790(1)-(N) and/or an intelligent storage array 795. SAN fabric 780 may also facilitate, via network 750 and servers 740 and 745, communication between client systems 710, 720, and 730 and storage devices 790(1)-(N) and/or intelligent storage array 795 in such a manner that devices 790(1)-(N) and array 795 appear as locally attached devices to client systems 710, 720, and 730. As with storage devices 760(1)-(N) and storage devices 770(1)-(N), storage devices 790(1)-(N) and intelligent storage array 795 generally represent any type or form of storage device or medium capable of storing data and/or other computer-readable instructions.

In certain embodiments, and with reference to exemplary computing system 610 of FIG. 6, a communication interface, such as communication interface 622 in FIG. 6, may be used to provide connectivity between each client system 710, 720, and 730 and network 750. Client systems 710, 720, and 730 may be able to access information on server 740 or 745 using, for example, a web browser or other client software. Such software may allow client systems 710, 720, and 730 to access data hosted by server 740, server 745, storage devices 760(1)-(N), storage devices 770(1)-(N), storage devices 790 (1)-(N), or intelligent storage array 795. Although FIG. 7 depicts the use of a network (such as the Internet) for exchanging data, the embodiments described and/or illustrated herein are not limited to the Internet or any particular network-based environment.

In at least one embodiment, all or a portion of one or more of the exemplary embodiments disclosed herein may be encoded as a computer program and loaded onto and executed by server 740, server 745, storage devices 760(1)-(N), storage devices 770(1)-(N), storage devices 790(1)-(N), intelligent storage array 795, or any combination thereof. All or a portion of one or more of the exemplary embodiments disclosed herein may also be encoded as a computer program, stored in server 740, run by server 745, and distributed to client systems 710, 720, and 730 over network 750. Accordingly, network architecture 700 may perform and/or be a means for performing, either alone or in combination with other elements, one or more of the detecting, measuring, using, determining, identifying, preventing, displaying, and modifying steps disclosed herein. Network architecture 700 may also be used to perform and/or be a means for performing other steps and features set forth in the instant disclosure.

As detailed above, computing system 610 and/or one or more components of network architecture 700 may perform and/or be a means for performing, either alone or in combination with other elements, one or more steps of an exemplary method for ensuring that critical computing decisions are intentionally made. In one example, such a method may include (1) detecting a request from a user to perform a computing act, (2) measuring, using a biofeedback sensor coupled to the computing device, physiological activity of the user that is indicative of a concentration level of the user, (3) determining, based on the measured physiological activity of the user, the user's concentration level, (4) identifying a requisite concentration level associated with the requested computing act, (5) determining whether the user's concentration level satisfies the requisite concentration level associated with the requested computing act, and then (6) preventing the requested computing act from occurring if the user's concentration level fails to satisfy the requisite concentration level associated with the requested computing act.

In some examples, detecting the request from the user to perform the computing act may include detecting an attempt by the user to respond to a user interface prompt associated with the requested computing act. In addition, measuring physiological activity of the user that is indicative of the user's concentration level may include measuring, using the biofeedback sensor coupled to the computing device, electrical activity produced by the user's brain.

In one example, the biofeedback sensor may include an EEG. In an additional example, the biofeedback sensor may represent a portion of a user input device coupled to the computing device.

In one embodiment, determining whether the user's concentration level satisfies the requisite concentration level associated with the requested computing act may include determining that the user's concentration level fails to satisfy the requisite concentration level associated with the requested computing act. The method may also include, upon determining that the user's concentration level fails to satisfy the requisite concentration level associated with the requested computing act, displaying a user interface prompt in an attempt to raise the user's concentration level and/or preventing the requested computing act from occurring. In this example, displaying the user interface prompt may include displaying the user interface prompt until the user provides a desired response and/or until the user's concentration level satisfies the requisite concentration level associated with the requested computing act. The method may also include modifying at least one characteristic of the user interface prompt in an attempt to raise the user's concentration level.

All or a portion of the method may be performed by an application and/or operating system installed on the computing device.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

In some examples, all or a portion of exemplary system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

While various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

In addition, one or more of the modules described herein may transform data, physical devices, and/or representations of physical devices from one form to another. For example, modules 102 in FIG. 1 may transform computing device 202 into a device capable of ensuring that critical computing decisions are intentionally made.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A computer-implemented method for ensuring that critical computing decisions are intentionally made, at least a portion of the method being performed by a computing device comprising at least one processor, the method comprising:

detecting, by the computing device, a request from a user to perform a computing act;

measuring, using a biofeedback sensor coupled to the computing device, physiological activity of the user that is indicative of a concentration level of the user;

determining, based on the measured physiological activity of the user, the user's concentration level;

identifying, by the computing device, a requisite concentration level associated with the requested computing act;

determining, by the computing device, whether the user's concentration level satisfies the requisite concentration level associated with the requested computing act;

preventing, by the computing device, the requested computing act from occurring if the user's concentration level fails to satisfy the requisite concentration level associated with the requested computing act.

2. The method of claim 1, wherein detecting the request from the user to perform the computing act comprises detecting an attempt by the user to respond to a user interface prompt associated with the requested computing act.

3. The method of claim 1, wherein measuring physiological activity of the user that is indicative of the user's concentration level comprises measuring, using the biofeedback sensor coupled to the computing device, electrical activity produced by the user's brain.

4. The method of claim 1, wherein the biofeedback sensor comprises an electroencephalograph.

5. The method of claim 1, wherein the biofeedback sensor comprises a portion of a user input device coupled to the computing device.

6. The method of claim 1, wherein determining whether the user's concentration level satisfies the requisite concentration level associated with the requested computing act comprises determining that the user's concentration level fails to satisfy the requisite concentration level associated with the requested computing act.

7. The method of claim 6, further comprising, upon determining that the user's concentration level fails to satisfy the requisite concentration level associated with the requested computing act, at least one of:
   displaying, by the computing device, a user interface prompt in an attempt to raise the user's concentration level;
   preventing, by the computing device, the requested computing act from occurring.

8. The method of claim 7, wherein displaying the user interface prompt comprises at least one of:
   displaying the user interface prompt until the user provides a desired response;
   displaying the user interface prompt until the user's concentration level satisfies the requisite concentration level associated with the requested computing act.

9. The method of claim 7, further comprising modifying, by the computing device, at least one characteristic of the user interface prompt in an attempt to raise the user's concentration level.

10. The method of claim 1, wherein at least a portion of the method is performed by at least one of:
   an application installed on the computing device;
   an operating system installed on the computing device.

11. A system for ensuring that critical computing decisions are intentionally made, the system comprising:
   a detection module programmed to detect a request from a user to perform a computing act;
   a concentration-evaluation module programmed to:
   measure, using a biofeedback sensor coupled to the computing device, physiological activity of the user that is indicative of a concentration level of user;
   determine, based on the measured physiological activity of the user, the user's concentration level;
   identify a requisite concentration level associated with the requested computing act;
   determine whether the user's concentration level satisfies the requisite concentration level associated with the requested computing act;
   a security module programmed to prevent the requested computing act from occurring if the user's concentration level fails to satisfy the requisite concentration level associated with the requested computing act;
   at least one processor configured to execute the detection module, the concentration-evaluation module, and the security module.

12. The system of claim 11, wherein the detection module detects the request from the user to perform the computing act by detecting an attempt by the user to respond to a user interface prompt associated with the requested computing act.

13. The system of claim 11, wherein the concentration-evaluation module measures physiological activity of the user that is indicative of the user's concentration level by measuring, using the biofeedback sensor coupled to the computing device, electrical activity produced by the user's brain.

14. The system of claim 11, wherein the biofeedback sensor comprises an electroencephalograph.

15. The system of claim 11, wherein the biofeedback sensor comprises a portion of a user input device coupled to the computing device.

16. The system of claim 11, wherein the concentration-evaluation module determines whether the user's concentration level satisfies the requisite concentration level associated with the requested computing act by determining that the user's concentration level fails to satisfy the requisite concentration level associated with the requested computing act.

17. The system of claim 16, wherein the security module is further programmed to at least one of:
   display a user interface prompt in an attempt to raise the user's concentration level;
   prevent the requested computing act from occurring.

18. The system of claim 17, wherein the security module displays the user interface prompt by at least one of:
   displaying the user interface prompt until the user provides a desired response;
   displaying the user interface prompt until the user's concentration level satisfies the requisite concentration level associated with the requested computing act.

19. The system of claim 17, wherein the security module is further programmed to modify at least one characteristic of the user interface prompt in an attempt to raise the user's concentration level.

20. A non-transitory computer-readable-storage medium comprising one or more computer-executable instructions that, when executed by at least one processor of a computing device, cause the computing device to:
   detect a request from a user to perform a computing act;
   measure, using a biofeedback sensor coupled to the computing device, physiological activity of the user that is indicative of a concentration level of the user;
   determine, based on the measured physiological activity of the user, the user's concentration level;
   identify a requisite concentration level associated with the requested computing act;
   determine whether the user's concentration level satisfies the requisite concentration level associated with the requested computing act;
   prevent the requested computing act from occurring if the user's concentration level fails to satisfy the requisite concentration level associated with the requested computing act.

* * * * *

UNITED STATES PATENT AND TRADEMARK OFFICE
CERTIFICATE OF CORRECTION

PATENT NO.        : 8,938,369 B1
APPLICATION NO.   : 13/048122
DATED             : January 20, 2015
INVENTOR(S)       : William E. Sobel Page 1 of 1

It is certified that error appears in the above-identified patent and that said Letters Patent is hereby corrected as shown below:

In the Claims,

Claim 11, at column 15, line 56, should read:

indicative of a concentration level of the user;

Signed and Sealed this
Twenty-first Day of July, 2015

Michelle K. Lee
*Director of the United States Patent and Trademark Office*